(12) United States Patent
Hantash (10) Patent No.: US 7,902,329 B2
(45) Date of Patent: Mar. 8, 2011

(54) OLIGOPEPTIDE TYROSINASE INHIBITORS AND USES THEREOF

(75) Inventor: Basil M. Hantash, East Palo Alto, CA (US)

(73) Assignee: The Board of Trustees of the Leland Stanford Junior University, Palo Alto, CA (US)

(*) Notice: Subject to any disclaimer, the term of this patent is extended or adjusted under 35 U.S.C. 154(b) by 181 days.

(21) Appl. No.: 12/146,070

(22) Filed: Jun. 25, 2008

(65) Prior Publication Data

US 2009/0099091 A1    Apr. 16, 2009

Related U.S. Application Data

(60) Provisional application No. 60/937,392, filed on Jun. 27, 2007.

(51) Int. Cl.
*A61K 38/00*   (2006.01)
*C07K 5/00*    (2006.01)
*C07K 7/00*    (2006.01)
*C07K 16/00*   (2006.01)
*C07K 17/00*   (2006.01)

(52) U.S. Cl. .................. 530/326; 530/327; 530/328

(58) Field of Classification Search .................. None
See application file for complete search history.

(56) References Cited

U.S. PATENT DOCUMENTS

| | | | |
|---|---|---|---|
| 3,755,560 A | 8/1973 | Dickert et al. | |
| 3,978,427 A | 8/1976 | Truscott | |
| 4,421,769 A | 12/1983 | Dixon et al. | |
| 4,522,752 A | 6/1985 | Sisto et al. | |
| 4,554,101 A | 11/1985 | Hopp | |
| 5,126,327 A | 6/1992 | Takeuchi et al. | |
| 5,455,228 A | 10/1995 | Coller et al. | |
| 5,543,389 A | 8/1996 | Yatvin et al. | |
| 5,589,460 A | 12/1996 | Abajian et al. | |
| 5,773,291 A | 6/1998 | Bouchard et al. | |
| 5,789,382 A | 8/1998 | Wellstein | |
| 5,854,204 A | 12/1998 | Findeis et al. | |
| 5,962,417 A | 10/1999 | Gilchrest | |
| 6,143,723 A * | 11/2000 | Ramaiah | 514/21 |
| 6,165,982 A | 12/2000 | Yamada et al. | |
| 6,256,533 B1 | 7/2001 | Yuzhakov et al. | |
| 6,283,978 B1 * | 9/2001 | Cheski et al. | 606/131 |
| 6,287,590 B1 | 9/2001 | Dasseux | |
| 6,323,219 B1 | 11/2001 | Costanzo et al. | |
| 6,602,856 B1 | 8/2003 | Quillan et al. | |
| 6,663,659 B2 * | 12/2003 | McDaniel | 607/88 |
| 6,695,853 B2 | 2/2004 | Karasiuk | |
| 6,858,581 B2 | 2/2005 | Kuhner et al. | |
| 6,982,249 B1 | 1/2006 | Schmaier et al. | |
| 7,025,957 B2 | 4/2006 | Arquette | |
| 7,083,781 B2 | 8/2006 | Fotinos | |
| 7,125,572 B2 | 10/2006 | Lee | |
| 2002/0192738 A1 | 12/2002 | Brissette et al. | |
| 2004/0086560 A1 | 5/2004 | Chaudhuri et al. | |
| 2004/0175767 A1 | 9/2004 | Orlow et al. | |
| 2006/0188462 A1 | 8/2006 | Bissett et al. | |
| 2007/0088371 A1 | 4/2007 | Karasiuk | |

FOREIGN PATENT DOCUMENTS

| | | |
|---|---|---|
| WO | 9858967 A1 | 12/1998 |
| WO | 2007001868 A1 | 1/2007 |

OTHER PUBLICATIONS

Hruby. Designing peptide receptor agonists and antagonists. Nature Reviews. Drug Discovery. Nov. 2002, vol. 1, pp. 847-858.*
Giebel, Lutz B., et al., "Tyrosinase Gene Mutations Associated with Type IB ("Yellow") Oculocutaneous Albinism," Am. J. Hum. Genet., 1991, 48:1159-1167.
Scott, Charles P., et al., "Production of cyclic peptides and proteins in vivo," Proc. Natl. Acad. Sci, Nov. 23, 1999, vol. 96, No. 24, 13638-13643.
Ohguchi, Kenji, et al., "Gnetol as a Potent Tyrosinase Inhibitor from Genus *Gnetum*," Biosci. Biotechnolo. Biochem., 2003, vol. 67, No. 3, 663-665.
Piao, Long Zhu, et al., "Mushroom Tyrosinase Inhibition Activity of Some Chromosomes," Chem. Pharm. Bull., 2002, vol. 50, No. 3, 309-311.
Al-Obeidi, et al., "Synthesis and Biological Activities of Fatty Acid Conjugates of a Cyclic Lactam a-Melanotropin," J. Med. Chem., 1992, vol. 35, 118-123.
Scimonelli, et al., "Inhibition by L-Protyl-L-Leucyl-Glycinamide (PLG) of Alpha-melanocyte stimulating hormone release from hypothalamic slices," Peptides, Nov. 1992, vol. 3, No. 6, 885-889. (Abstract).
Fletcher, et al., "Partially Modified Retro-Inverso Peptides: Development, Synthesis, and Conformational Behavior," Chemical Reviews, Mar. 1998, vol. 98, 763-795.
PCT/3815.41A-1 International Search Report, mailed Oct. 22, 2008.
PCT/3815.41A-1 Written Opinion of the International Searching Authority, mailed Oct. 22, 2008.
PCT/3815.41B-1 International Search Report, mailed Nov. 14, 2008.
PCT/3815.41B-1 Written Opinion of the International Searching Authority, mailed Nov. 14, 2008.

* cited by examiner

*Primary Examiner* — Marcela M Cordero Garcia
(74) *Attorney, Agent, or Firm* — David J. Aston; Peters Verny, LLP (57) ABSTRACT

Disclosed are peptides that inhibit the enzymatic activity of tyrosinase, as well as formulations and methods for their use in the reduction of skin pigmentation, and methods of administering the inhibitory peptides in a topical formulation. Peptide sequences disclosed include KFEKKFEK and YRSRKYSSWY.

11 Claims, 5 Drawing Sheets

SEQUENCE LISTING

```
<160> NUMBER OF SEQ ID NOS: 5

<210> SEQ ID NO 1
<211> LENGTH: 8
<212> TYPE: PRT
<213> ORGANISM: artificial
<220> FEATURE:
<223> OTHER INFORMATION: synthetic peptide

<400> SEQUENCE: 1

Lys Phe Glu Lys Lys Phe Glu Lys
1               5

<210> SEQ ID NO 2
<211> LENGTH: 10
<212> TYPE: PRT
<213> ORGANISM: Artificial
<220> FEATURE:
<223> OTHER INFORMATION: Synthetic peptide

<400> SEQUENCE: 2

Tyr Arg Ser Arg Lys Tyr Ser Ser Trp Tyr
1               5                   10

<210> SEQ ID NO 3
<211> LENGTH: 4
<212> TYPE: PRT
<213> ORGANISM: Artificial
<220> FEATURE:
<223> OTHER INFORMATION: Synthetic peptide

<400> SEQUENCE: 3

Val Leu Leu Lys
1

<210> SEQ ID NO 4
<211> LENGTH: 8
<212> TYPE: PRT
<213> ORGANISM: Artificial
<220> FEATURE:
<223> OTHER INFORMATION: Synthetic peptide

<400> SEQUENCE: 4

Lys Phe Glu Phe Lys Phe Glu Phe
1               5
```

```
<210> SEQ ID NO 5
<211> LENGTH: 10
<212> TYPE: PRT
<213> ORGANISM: Artificial
<220> FEATURE:
<223> OTHER INFORMATION: Synthetic peptide

<400> SEQUENCE: 5

Tyr Arg Ser Arg Lys Tyr Ser Ser Trp Tyr
1               5                   10
```

OLIGOPEPTIDE TYROSINASE INHIBITORS AND USES THEREOF

CROSS-REFERENCE TO RELATED APPLICATIONS

This application claims priority from U.S. Provisional Patent Application No. 60/937,392, filed on Jun. 27, 2007, which is hereby incorporated by reference in its entirety.

STATEMENT OF GOVERNMENTAL SUPPORT

None.

REFERENCE TO SEQUENCE LISTING, COMPUTER PROGRAM, OR COMPACT DISK

Applicants assert that the paper copy of the Sequence Listing is identical to the Sequence Listing in computer readable form found on the accompanying computer disk. Applicants incorporate the contents of the sequence listing by reference in its entirety.

BACKGROUND OF THE INVENTION

1. Field of the Invention

The present invention relates to the field of tyrosinase inhibitors and to methods and compositions of treatment involving inhibition of this enzyme.

2. Related Art

The present invention relates to novel biological agents, specifically oligopeptides that reduce the enzymatic activity of tyrosinase. These agents have use as research and development tools in basic science investigation, in diagnostic applications, as cosmeceuticals for the treatment of skin conditions characterized by hyperpigmentation, and as therapeutics for the treatment of pathological conditions that rely on tyrosinase enzyme activity to promote their tumorigenicity.

Melanin plays an important role in protecting the human body from the harmful effects of ultraviolet rays. Melanin is also an important factor in medical science and cosmetology. It is known that melanin is formed or synthesized in skin tissues. Excessive amounts of melanin darken the skin, and the nonuniform distribution of melanin causes chloasma and ephelis, both of which are skin disorders. The biosynthesis pathway of melanin involves the catalytic hydroxylation of tyrosine to L-3,4-dihydroxyphenylalanine (L-DOPA) and the conversion of L-DOPA to dopachrome. An effective way to inhibit the synthesis of melanin is to block the hydroxylation of tyrosine.

Hydroquinone (HQ) has been used since the 1950s in commercially available over-the-counter skin lightener products and since the 1960s as a commercially available medical product. It is also used in cosmetic products such as hair dyes and products for coating fingernails. Beginning in 2001, HQ is no longer authorized for use in cosmetic skin lightening formulations in European Union countries, although products containing arbutin, an analogue of HQ, and botanicals, including plants that naturally contain HQ and arbutin, continue to remain available in European countries See also, Matsubayashi et al., "Pharmaceutical and clinical assessment of hydroquinone ointment prepared by extemporaneous nonsterile compounding," Biol Pharm Bull. 2002 January; 25(1): 92-6. As disclosed there, ointments of the skin depigmentation agent hydroquinone (HQ) have been prepared by extemporaneous nonsterile compounding in Japan by imitating skin lightening creams commercially available in the U.S.A. and European Union. However, various problems have been observed including chromatic aberration of HQ ointments, relatively large variability of efficacy, and undesirable side effects although they were mild. HQ has a published IC50 of about 700 µM.

Therapies containing hydroquinone have been outlawed in Asian countries, making the standard HQ treatment inaccessible to a large number of people suffering from this condition. In fact, the United States FDA has issued a notice indicating that it may too ban the use of hydroquinone domestically. Furthermore, hydroquinone has been associated with visceral malignancy and long-term topical delivery may be a potentially harmful therapeutic option. Hydroquinone in the best of circumstances leads to only a partial alleviation of hyperpigmentation. Some cosmeceutical formulations have included other active ingredients such as kojic acid, arbutin, and vitamin C but efficacy has thus far been disappointing due to problems with chemical instability or inability to deliver the active to the appropriate layer of skin. Although higher concentrations have been utilized, patients often discontinue treatment due to skin irritation. This led to the addition of topical steroids in order to reduce irritation from the active ingredients such as retin A and hydroquinone. Since melasma and other hyperpigmentary disorders often take months to years to treat, use of topical steroids on the face at the strength required to combat irritant effects of active ingredients is not possible without causing topical steroid-induced side effects. When medium or greater potency topical steroids are used on the face for more than several weeks consecutively, skin atrophy, fragility and telengiectasia commonly occur. This side effect profile is unacceptable, especially in areas such as the face.

Infrared lasers have been used with some success. They generally are more effective for conditions that localize pigment to the deeper skin areas such as the dermis. In order to effectively treat the epidermis, an ablative treatment is usually employed. This therapy is associated with significant downtime for the patient, including creation of second-degree burn or erosion leaving the patient susceptible to infection. In addition, laser therapy is an expensive treatment option that many patients cannot afford. In extreme cases, depigmentation of the skin has been elected when bleaching agents have been unsuccessful. Numerous pathological conditions can lead to the deposition of pigment into the skin aberrantly. For example, it is well known that hormonal imbalance can cause facial and extremity hyperpigmentation, most frequently observed in women during or following pregnancy. Often times, this hyperpigmentation becomes aesthetically disfiguring, leading to problems with self-esteem and embarrassment in social situations. Melasma often times affects individuals with Fitzpatrick type IV-VI skin. This constitutes a significant portion of the worldwide population.

A large number of individuals with Fitzpatrick type IV to VI skin are of Asian descent.

According to the Fitzpatrick skin type scale, based on a test of appearance and skin reaction to sun exposure, individuals are generally categorized as follows:

Type I: Very fair skin tone, blond or redhead,
Type II: Light skin tone, will tan, but usually burns.
Type III: White to olive skin tone, sometimes burns.
Type IV: Medium brown skin tone, rarely burns.
Type V: Dark brown skin tone, very rarely burns.
Type VI: Black skin tone, very dark eyes, burn resistant.

In addition to melasma, hyperpigmentation of aesthetically sensitive locations such as the face may take place after inflammation due to disorders such as acne or rosacea, amongst others. These conditions may also lead to significant psychological discomfort. In the United States, $13 billion are spent on cosmeceuticals each year. With the anticipated ban of hydroquinone in the US market, in conjunction with the continued stability (vitamin C) or delivery (arbutin, kojic acid, etc) problems of other non-pharmacological agents currently on the market, oligopeptide inhibitors may provide a solution to this large unmet need.

SPECIFIC PATENTS AND PUBLICATIONS

Scot et al., "Production of cyclic peptides and proteins in vivo," *Proc. Nat. Acad. Sci. Vol.* 96, Issue 24, 13638-13643, Nov. 23, 1999, discloses the production of the cyclic, eight-amino acid tyrosinase inhibitor pseudostellarin F in bacteria.

Verma et al., "Modulation of agonist binding to human dopamine receptor subtypes by L-prolyl-L-leucyl-glycinamide and a peptidomimetic analog," *J Pharmacol Exp Ther.* 2005 December; 315(3):1228-36. Epub 2005 Aug. 26, discloses the role of the hypothalamic tripeptide L-prolyl-L-leucyl-glycinamide (PLG) and its conformationally constrained analog 3(R)-[(2(S)-pyrrolidinylcarbonyl)amino]-2-oxo-1-pyrrolidineacetamide (PAOPA) in modulating agonist binding to human dopamine (DA) receptor subtypes.

U.S. Pat. No. 6,165,982 to Yamada, et al., issued Dec. 26, 2000 entitled "Use of sericin as antioxidants and tyrosinase inhibitors," discloses a composition useful as an antioxidant or an inhibitor for tyrosinase activity which comprises as an active ingredient a sufficient amount of sericin to exert an antioxidizing ability. Sericin is a high molecular weight, natural, soluble glycoprotein constituent of silk. Sericin binds to the keratin of skin and hair, forming a protective film.

U.S. Pat. No. 5,126,327 to Takeuchi, et al., issued Jun. 30, 1992, entitled "Melanocyte-stimulating hormone inhibitor and external preparation containing the same," discloses a melanocyte-stimulating hormone inhibitor which has certain amino acid sequences, an acyl group having 1 to 12 carbon atoms, an amino acid residue, or acylated derivative thereof having 1 to 12 carbon atoms, peptide residue having 2 to 40 amino acid residues or acylated derivative thereof.

U.S. Pat. No. 7,025,957 to Arquette, issued Apr. 11, 2006, entitled "Composition and method to whiten skin," discloses a composition effective as a skin whitening agent. The composition includes Simmondsin, which is a glycoside extracted from jojoba meal (Simmondsia chinensis). In certain embodiments, the composition comprises an extract of jojoba (Simmondsia chinensis). The composition is administered by topically applying to an individual a formulation in an amount effective to whiten skin, where that composition comprises a jojoba extract.

U.S. Pat. No. 7,083,781 to Fotinos, et al., issued Aug. 1, 2006, entitled "Film forming polymers, methods of use, and devices and applications thereof," discloses compositions and methods for delivering active agents to the skin of a subject, including a polymer, an active ingredient and a solvent, the compositions being capable of delivery by rolling, spreading, aerosol or in droplets and of forming a film in contact with the skin. A cosmetic active agent known in the art may be incorporated in the film forming compositions for improving skin appearance. Anti-hyperpigmentation agents typically used for counterbalancing this condition can include tyrosinase inhibitors such as peptide mixtures and plant extracts, fermentation products, and antioxidants such as hydroquinone, kojic acid, ascorbic acid derivatives, synthetic or natural derivatives of hydroquinone and hydroquinone precursors. In preferred embodiments of the invention, anti-hyper pigmentation agents are Melawhite of Pentharm Ltd., Basel, Switzerland; Biowhite™ of Coletica, France; Etioline of Sederma, France; Arbossa of Kelesima, Italy; Gatuline whitening of Gattefosse, France; Ascorbocilan C of Exsymol, Monaco; and Kojic acid of Alps Pharm., Japan.

U.S. Pat. No. 7,125,572 to Lee, issued Oct. 24, 2006, entitled "Tyrosinase inhibitor extract," discloses a tyrosinase inhibitor extract from lemon peels. The tyrosinase inhibitor provides advantageous skin whitening effects. According to the invention, the tyrosinase inhibitor extract of the invention has a main absorbance at 280 nm. This indicates that the tyrosinase inhibitor extract contains a protein or peptide. It is believed that the protein or peptide is the main active component for inhibiting tyrosinase. The other components of the extract may provide additional effects such as anti-aging and anti-oxidation. The tyrosinase inhibitor extract can be prepared to be in various forms, including lotions, emulsions, creams, ointments, sticks, solutions, packs, and gel. The tyrosinase inhibitor extract may be admixed with any ingredients ordinarily used in cosmetics, such as oily substances, humectants, thickeners, preservatives, emulsifiers, medical ingredients, perfumes, emulsification stabilizers and the like.

U.S. Pat. No. 6,143,723 to Ramaiah teaches that a peptide according to the YR sequence below enhances skin pigmentation, rather than reducing it, as is demonstrated herein.

Various other patents and publications disclose unrelated peptides. See, e.g., U.S. Pat. No. 5,789,382, which discloses TyrArgSerArgLysTyrSerSerTrpTyr (SEQ ID NO: 5) as a blocking peptide for FGF receptor.

BRIEF SUMMARY OF THE INVENTION

The following brief summary is not intended to include all features and aspects of the present invention, nor does it imply that the invention must include all features and aspects discussed in this summary.

The present invention concerns certain peptide sequences exemplified as:

```
                                        >1 SEQ ID NO: 1
                    KFEKKFEK (KF peptide)

>2 SEQ ID NO: 2
                    YRSRKYSSWY (YR peptide)
```

The present invention is further directed to kits and compositions containing the present peptides, and methods of treatment of conditions involving expression of tyrosinase, in which the present peptides are administered topically for the treatment of conditions involving melanocyte activity in the skin. Other formulations are useful in treating tyrosinase activity in other regions of the body and may be administered internally.

Thus, in certain aspects, the present invention is directed to a purified peptide having at least 63% identity to an amino acid sequence KFEKKFEK (SEQ ID NO: 1), and having an IC 50 of tyrosinase of less than about 10 mM. The peptide in effect may be substituted in up to three positions, including deletions. Guidance is given for making these alterations, as well as testing them for inhibitory potency. In some cases, the peptide will have an IC50 of less than about 5 mM, or even less. In some cases, it is within the present invention to substitute a residue with R or F, in that these residues serve to increase peptide binding to the tyrosinase. Thus, it is preferred that the residue substituted with R or F not be an F; if it is, it would be substituted with R. Similarly, in the case of YRSRKYSSWY (SEQ ID NO: 2), the residue substituted would preferably not be R. Between one and three residues may be substituted with V, A, L, M or I, in that these residues serve to increase inhibitory function. In addition, one may substitute K with L or R; F with W or Y; E with D, as it is known that these residues are similar. It is also advantageous in some embodiments to have two adjacent charged amino acids. In certain aspects, the invention comprises the use of D-amino acids for some or all of the amino acids. The peptides may be linked to a modulating group, as defined below, such as palmitic acid or ester. The peptide may have two adjacent charged amino acids.

In certain aspects, the present substitutions may be presented in table form:

| Column 1-recited residue | Column 2-new residue |
|---|---|
| K | L or R |
| F | W or Y |
| E | D |

In certain aspects, the present invention comprises a topical formulation useful in skin whitening. The formulation is made from dermatologically acceptable ingredients. The formulation may comprise standard carrier material, as well as in certain cases, a secondary treatment agent and a peptide essentially identical to a sequence selected from the group consisting of YRSRKYSSWY (SEQ ID NO: 2) and KFEKKFEK (SEQ ID NO: 1). These peptides may be altered as described above. In certain embodiments, the formulations may be adapted for potential over the counter use, or for prescription use. For over the counter use, one may employ a formulation wherein the peptide is at a concentration less than about two times the IC 50 concentration. For pharmaceutical use, one may the peptide may be at a concentration of two to 100 times the IC 50 concentration.

The present peptides are in certain aspects superior to HQ, and may be formulated to be substantially free of HQ. In certain formulations, different peptides may be combined, with different sequences, different attached groups, and so forth. The carrier may include a material selected from: hydrating formulations, antioxidant formulations, and free radical scavengers.

In certain formulations, the peptides will have improved skin uptake by being formulated in liposomes.

In certain aspects, the present invention comprises methods of skin treatment, involving skin lightening (whitening). This aspect includes a method for treatment of skin comprising administering to the skin a peptide essentially identical to one of: (a) KFEKKFEK (SEQ ID NO: 1) or (b) YRSRKYSSWY (SEQ ID NO: 2), wherein said administering of the peptide inhibits tyrosinase sufficiently to lighten skin pigmentation. The administering may comprise administering a topical preparation, as referred to above, and may further comprise a secondary treatment product.

The present methods of treatment also include carrying out the skin whitening with further assistance from a microdermabrasion process. The administering may be simultaneous with the microdermabrasion process. The administering is in conjunction with a radiation process. Such processes may be used to increase skin permeability. Furthermore, the administering may be in conjunction with a physical treatment carried out by an abrading device a microneedle, an electroporation device, or an iontophoretic device.

In certain aspects, the present invention comprises a kit for carrying out a skin whitening procedure, comprising a purified peptide having an IC 50 of tyrosinase of less than about 10 mM and selected from the group consisting of: a peptide having and a sequence at least 63% identical to the sequence of either YR peptide or KF peptide; a dermatologically acceptable carrier; a secondary treatment product; and directions for use. The kit may be aimed at consumers or physicians, and may include a precombination of the peptide and carrier, such that the formulation is ready to apply, or it may require mixing of the peptide with the carrier.

DETAILED DESCRIPTION OF THE PREFERRED EMBODIMENT

Overview

Short peptides of between about 6 and 12 amino acids are disclosed and shown to have inhibitory activity against tyrosinase. Short sequence peptides are synthetically designed in certain embodiments using naturally occurring amino acids, and therefore are biologically safe. They can be delivered to melanocytes through a number of mechanisms, including but not limited to liposomes, allowing access to the appropriate skin layer. These peptides do not suffer from oxidation problems, as does the most commonly used ingredient vitamin C. These peptides do not cause liver cancer, as does hydroquinone, and since they are derived from naturally occurring amino acids, are easily degraded intracellularly upon inactivation of tyrosinase. They cause skin lightening or whitening by inhibiting the synthesis of melanin.

Definitions

Unless defined otherwise, all technical and scientific terms used herein have the same meaning as commonly understood by those of ordinary skill in the art to which this invention belongs. Although any methods and materials similar or equivalent to those described herein can be used in the practice or testing of the present invention, the preferred methods and materials are described. Generally, nomenclatures utilized in connection with, and techniques of, cell and molecular biology and chemistry are those well known and commonly used in the art. Certain experimental techniques, not specifically defined, are generally performed according to conventional methods well known in the art and as described in various general and more specific references that are cited and discussed throughout the present specification. For purposes of the clarity, following terms are defined below.

The term "tyrosinase" is used herein to refer to monophenol monooxygenase (EC 1.14.18.1; CAS number: 9002-10-2), an enzyme that catalyses the oxidation of phenols (such as tyrosine). It is a copper-containing enzyme present in plant and animal tissues that catalyzes the production of melanin and other pigments from tyrosine by oxidation. All tyrosinases have in common a binuclear type-3 copper center within their active site. Here two copper atoms are each coordinated with three histidine residues. Matoba et al., "Crystallographic evidence that the dinuclear copper center of tyrosinase is flexible during catalysis," *J Biol Chem.*, 2006 Mar. 31; 281(13):8981-90. Epub 2006 Jan. 25, disclose a three-dimensional model of a tyrosinase catalytic center.

The term "peptide" is used herein in its conventional sense, i.e., a polymer in which the monomers are amino acids and are joined together through amide bonds, alternatively referred to as a polypeptide. When the amino acids are α-amino acids, either the L-optical isomer or the D-optical isomer may be used. Additionally, unnatural amino acids, for example, β-alanine, phenylglycine and homoarginine are also meant to be included. The present peptides are two or more amino acid monomers long and may be up to 20 amino acid monomers long. Standard abbreviations for amino acids are used (as described below).

The term "carrier" refers to compounds commonly used on the formulation of pharmaceutical compounds used to enhance stability, sterility and deliverability of the therapeutic tyrosinase inhibitor. When the peptide delivery system is formulated as a solution or suspension, the delivery system is in an acceptable carrier, preferably an aqueous carrier. A variety of aqueous carriers may be used, e.g., water, buffered water, 0.8% saline, 0.3% glycine, hyaluronic acid and the like. These compositions may be sterilized by conventional, well-known sterilization techniques, or may be sterile filtered. The resulting aqueous solutions may be packaged for use as is, or lyophilized, the lyophilized preparation being combined with a sterile solution prior to administration. The compositions may contain pharmaceutically acceptable auxiliary substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, triethanolamine oleate, etc.

The term "topical" or "topically" is used here in its conventional sense as referring to a spot, which can be in or on any part of the body, including but not limited to the epidermis, any other dermis, or any other body tissue. Topical administration or application means the direct contact of the peptide with tissue, such as skin or membrane, which contains melanin-producing cells. Methods of applying the present topical agents to the skin or mucosa include "non-finite" or liquid or semi-liquid carriers such as gels, lotions, emulsions, creams, plasters, or ointments, or "finite" carriers, non-spreading substances which retain their form, e.g., patches, dressings and bandages. The solvents for the finite and non-finite forms of the active peptides are non-toxic, pharmaceutically acceptable substances, preferably liquids, which do not substantially negatively affect the adhesion properties or solubility of the system. The solvent is preferably a polyhydric alcohol or combination of polyhydric alcohols. The term polyhydric alcohol means any organic polyalcohol and includes dipropylene glycol, propylene glycol, polyethylene glycol, glycerin, butylene glycol, hexylene glycol, polyoxyethylene, polypropylene glycol, sorbitol, ethylene glycol, and the like. Other suitable solvents include fatty acids such as oleic acid, linoleic acid, capric acid and the like, as well as fatty esters or alcohols. Further suitable solvents include other non-toxic, non-volatile solvents commonly used in dermal or transdermal compositions for dissolving peptide-based compositions.

The term "sequence identity" in the context of two polypeptide sequences refers to the residues in the two sequences, which are the same when aligned for maximum correspondence. Optimal alignment of sequences for comparison can be conducted, e.g., by the local homology algorithm of Smith and Waterman, *Adv. Appl. Math.* 2: 482 (1981), by the homology alignment algorithm of Needleman and Wunsch, *J. Mol. Biol.* 48:443 (1970), by the search for similarity method of Pearson and Lipman, *Proc. Natl. Acad. Sci.* (*U.S.A.*) 85: 2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by inspection. Sequence identity may be calculated on the basis of residues identical to a reference sequence. For example, for KFEKKFEK (SEP ID NO 1), having 8 residues one may have 5 identical residues and have 5/8 or 62.5 (63%) sequence identity. Because of the limited length of the peptides, at least 63% identity is considered "essentially identical" when changes are made according to the present teachings. One may also have 6/8 (75%) or 7/8 (88%) sequence identity. As a further example, a residue may be eliminated, such as E (glutamate) may be changed to V, L, M or I and one would have and have 7/8 or 88% identity. In the case of a method or formulation of the YR peptide, one may modify 3/10 residues, for 70% identity.

The terms "substantial identity" as used herein denotes a characteristic of a polypeptide sequence, wherein the polypeptide comprises a sequence that has at least 60 percent sequence identity, preferably at least 85 percent identity and often 90 to 95 percent sequence identity, more usually at least 99 percent sequence identity as compared to a reference sequence over a comparison window of the entire peptide length. Substantial identity further involves a conservative substitution of an amino acid. The term "essentially identical" in the context of the present 8 or 10 residue peptides means that three amino acid substitutions are permitted, according to the present teachings specifically providing guidance in making substitutions, and the definition above.

Conservative amino acid substitutions are those that take place within a family of amino acids that are related in their side chains. Genetically encoded amino acids are generally divided into families: (1) acidic=aspartate, glutamate; (2) basic=lysine, arginine, histidine; (3) non-polar-alanine, valine, leucine, isoleucine, proline, phenylalanine, methionine, tryptophan; and (4) uncharged polar=glycine, asparagine, glutamine, cysteine, serine, threonine, tyrosine. More preferred families are: serine and threonine are aliphatic-hydroxy family; asparagine and glutamine are an amide-containing family; alanine, valine, leucine and isoleucine are an aliphatic family; phenylalanine, tryptophan, and tyrosine are an aromatic family, and cysteine and methionine as a sulfur-containing side chain family. For example, it is reasonable to expect that an isolated replacement of a leucine with an isoleucine or valine, an aspartate with a glutamate, a threonine with a serine, or a similar replacement of an amino acid with a structurally related amino acid will not have a major effect on the binding or properties of the resulting molecule, especially if the replacement does not involve an amino acid within a framework site. Preferred conservative amino acid substitution groups are: valine-leucine-isoleucine, phenylalanine-tyrosine, lysine-arginine, alanine-valine, glutamic acid-aspartic acid, cysteine-methionine, and asparagine-glutamine.

As further guidance in making amino acid substitutions, one may substitute by changing a given residue to R, or F to increase binding properties, or change it to V, A, L, M or I to increase inhibitory properties. One may direct one part of the peptide to binding to the tyrosinase enzyme, and another part towards inhibition. It is generally preferred not to change F or R and to change K or E, as well as Y or W. Changes to Y should be considered in the context of the overall sequence, since t is the residue that is the natural substrate for tyrosinase. It should be noted that some changes may in fact result in an increase of tyrosinase activity. See, for further guidance, Schurink et al., "Novel peptides with tyrosinase inhibitory activity," Peptides 28:485:495 (January 2007).

The term "keratinous tissue," as used herein, refers to keratin-containing layers disposed as the outermost protective covering of mammals (e.g., humans, dogs, cats, etc.) which includes, but is not limited to, skin, mucosa, lips, hair, toenails, fingernails, cuticles, hooves, etc.

The term "topical application," as used herein, means to apply or spread the compositions of the present invention onto the surface of the keratinous tissue.

The term "dermatologically-acceptable," as used herein, means that the compositions or components thereof so described are suitable for use in contact with mammalian keratinous tissue without undue toxicity, incompatibility, instability, allergic response, and the like.

The term "injectable formulation," as used herein, means a formulation suitable for injection into humans and/or animals, wherein the injection is intradermal, subcutaneous, intramuscular or intravenous. These formulations will be sterile, pyrogen free, and at a physiologically acceptable pH.

The term "radiation process," as used herein, means a treatment process as applied to a subject's skin or internal tissue, and is used for cosmetic or therapeutic purposes. The term includes the use of electromagnetic radiation devices, such as lasers, LEDs, radiofrequency, etc. The term also includes the use of ultrasound devices. These devices all are used in processes in which skin whitening using the present agents may be carried out. Some of these processes alter the stratum corneum permeability, and would be beneficially useful in a process of administering the present peptides.

The term "IC 50," as is understood in the art, means the means the concentration of tyrosinase inhibitor peptide required to effect 50% inhibition of tyrosinase activity, as conducted in an in vitro assay; a value of "less than" a certain concentration includes IC 50 values at lower concentrations. The term about may encompass plus or minus 10% variation, and variations resulting from different reagents, experimental conditions, etc. In vitro determinations of IC 50 using a purified tyrosinase preparation (e.g., mushroom tyrosinase) are useful in determining a clinical dose.

General Method and Materials

The present materials and methods in a general sense are peptides, which inhibit tyrosinase activity and may be formulated for application to humans. They thus are useful in treatment or amelioration of conditions involving over production of melanin.
Peptides
The present peptides include peptide analogues or peptide derivatives or peptidomimetics that retain the ability to inhibit a tyrosinase activity within a cell. For example, an inhibitory peptide tyrosinase modulator of the invention may be modified to increase its stability, bioavailability, solubility, etc. The terms "peptide analogue," "peptide derivative" and "peptidomimetic" are used herein to include molecules that mimic the chemical structure of a peptide and retain the functional properties of the peptide. Approaches to designing peptide analogs are known in the art. For example, see Farmer, P. S. in Drug Design (E. J. Ariens, ed.) Academic Press, New York, 1980, vol. 10, pp. 119-143; Ball. J. B. and Alewood, P. F. (1990) J. Mol. Recognition 3:55; Morgan, B. A. and Gainor, J. A. (1989) Ann. Rep. Med. Chem. 24:243; and Freidinger, R. M. (1989) Trends Pharmacol. Sci. 10:270. Examples of peptide analogues, derivatives and peptidomimetics include peptides substituted with one or more benzodiazepine molecules (see e.g., James, G. L. et al. (1993) Science 260:1937-1942), peptides with methylated amide linkages and "retro-inverso" peptides (see U.S. Pat. No. 4,522,752 by Sisto). Peptide analogues, peptide derivatives and peptidomimetic are described in further detail below.

Peptides of the present invention may comprise residues from any of the naturally-amino acids, or from non-naturally-occurring amino acids. These naturally-occurring and non-naturally-occurring amino acids may be in the D or L configuration. The terms D and L are used herein as they are known to be used in the art. Peptides of the invention include single amino acids and short spans (e.g., 1-10) of amino acids. In addition, modified peptides of the present invention may also comprise a monomer or dimer.

The standard single letter and three letter codes for amino acids are used herein and are as follows:

| | | |
|---|---|---|
| A (Ala) Alanine | C (Cys) Cysteine | D (Asp) Aspartic acid |
| E (Glu) Glutamic acid | F (Phe) Phenylalanine | G (Gly) Glycine |
| H (His) Histidine | I (Ile) Isoleucine | K (Lys) Lysine |
| L (Leu) Leucine | M (Met) Methionine | N (Asn) Asparagine |
| P (Pro) Proline | Q (Gln) Glutamine | R (Arg) Arginine |
| S (Ser) Serine | T (Thr) Threonine | V (Val) Valine |
| W (Trp) Tryptophan | Y (Tyr) Tyrosine | |

As described above, the indicated residues may be the naturally occurring L amino acid, or a modification thereof, that is, a chemical modification, an optical isomer, or a link to a modifying group. It is contemplated that specific modifications may be made within the peptide that maintain the ability of the present peptides to specifically inhibit the activity of tyrosinase whereby it catalyzes the first two steps in the pathway for pigment synthesis: hydroxylation of the amino acid tyrosine into dihydroxyphenylalanine (DOPA) and/or the subsequent oxidation into dopaquinone It is also contemplated that specific modifications may be made in a particular sequence in order to confer some additional desirable property to the peptide. Certain amino acids may be substituted for other amino acids in a protein structure without appreciable loss of peptide activity. Since it is the interactive capacity and nature of a peptide that defines that peptide's biological functional activity, certain amino acid sequence substitutions can be made even in a short peptide sequence and nevertheless obtain a peptide with like properties. It is thus contemplated by the inventor that various changes may be made in the sequence of the present tyrosinase inhibitors without appreciable loss of biological utility or activity and perhaps may enhance desired activities.

For example, in designing peptide constructs with tyrosinase inhibitory properties, substitutions may be used which modulate one or more properties of the molecule. Such variants typically contain the exchange of one amino acid for another at one or more sites within the peptide. For example, certain amino acids may be substituted for other amino acids in a peptide structure in order to enhance the interactive binding capacity of the structures. One may also substitute D- for L-amino acids, or include certain side chain covalent modifications.

In making such changes, the hydropathic index of amino acids may be considered.

The importance of the hydropathic amino acid index in conferring interactive biologic function on a protein is generally understood in the art (Kyte and Doolittle, 1982). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like.

Each amino acid has been assigned a hydropathic index on the basis of their hydrophobicity and charge characteristics (Kyte and Doolittle, 1982), these are: isoleucine (+4.5); valine (+4.2); leucine (+3.8); phenylalanine (+2.8); cysteine/ cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

In modifying the presently exemplified sequences, certain amino acids may be substituted by other amino acids having a similar hydropathic index or score and still result in a protein with similar biological activity, i.e., still obtain a biological functionally equivalent protein. In making such changes, the substitution of amino acids whose hydropathic indices are within ±2 is preferred, those that are within ±1 are particularly preferred, and those within ±0.5 are even more particularly preferred.

Substitution of like amino acids can also be made effectively on the basis of hydrophilicity. U.S. Pat. No. 4,554,101, incorporated herein by reference, states that the greatest local average hydrophilicity of a protein, as governed by the hydrophilicity of its adjacent amino acids, correlates with a biological property of the protein. As detailed in U.S. Pat. No. 4,554, 101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4).

In modifying the exemplified sequences, amino acid substitutions may also be generally based on the relative similarity of the amino acid side-chain substituents, for example, their hydrophobicity, hydrophilicity, charge, size, and the like but may nevertheless be made to highlight a particular property of the peptide. Exemplary substitutions that take various of the foregoing characteristics into consideration are well known to those of skill in the art and include: arginine and lysine, which, with histidine, are basic at physiological pH; glutamate and aspartate (which are acidic); serine and threonine; glutamine and asparagine; and valine, leucine and isoleucine.

The naturally occurring amino acid side chains are illustrated below, in which * represents the attachment point to the compound's backbone:

The amino acids of the peptides of the present invention may also be modified so that amino groups may be acylated, alkylated or arylated. Benzyl groups may be halogenated, nitrosylated, alkylated, sulfonated or acylated.

Various chemically modified amino acids may be incorporated into the present peptides. Examples of these include:

Acetylated
  N-acetyl-L-alanine, N-acetyl-L-arginine; N-acetyl-L-asparagine; N-acetyl-L-aspartic acid; N-acetyl-L-cysteine; N-acetyl-L-glutamine; N-acetyl-L-glutamic acid; N-acetylglycine; N-acetyl-L-histidine; N-acetyl-L-isoleucine; N-acetyl-L-leucine; N2-acetyl-L-lysine; N6-acetyl-L-lysine; N-acetyl-L-methionine; N-acetyl-L-phenylalanine; N-acetyl-L-proline; N-acetyl-L-serine; N-acetyl-L-threonine; N-acetyl-L-tryptophan; N-acetyl-L-tyrosine; N-acetyl-L-valine.

Amidated
  L-alanine amide, L-arginine amide

Formylated
  N-formyl-L-methionine

Hydroxylated
  4-hydroxy-L-proline

Lipid Modified
  S-farnesyl-L-cysteine, S-geranylgeranyl-L-cysteine, N-palmitoyl-L-cysteine, S-palmitoyl-L-cysteine, N-myristoyl-glycine, N6-myristoyl-L-lysine Methylated
  N-methyl-L-alanine, N,N,N-trimethyl-L-alanine, omega-N,omega-N-dimethyl-L-arginine L-beta-methylthioaspartic acid, N5-methyl-L-glutamine, L-glutamic acid 5-methyl ester 3'-methyl-L-histidine, N6-methyl-L-lysine, N6,N6-dimethyl-L-lysine, N6,N6,N6-trimethyl-L-lysine, N-methyl-L-methionine, N-methyl-L-phenylalanine Phosphorylated omega-N-phospho-L-arginine, L-aspartic 4-phosphoric anhydride, S-phospho-L-cysteine, 1'-phospho-L-histidine, 3'-phospho-L-histidine, O-phospho-L-serine, O-phospho-L-threonine, O4'-phospho-L-tyrosine Other L-selenocysteine, L-selenomethionine, L-3-oxoalanine, 2-pyrrolidone-5-carboxylic acid, L-glutamyl 5-glycerylphosphorylethanolamine, 2'-[3-carboxamido-3-(trimethylammonio)propyl]-L-histidine (diphthamide), N6-biotinyl-L-lysine, N6-(4-amino-2-hydroxybutyl)-L-lysine (hypusine), N6-retinal-L-lysine Other modifications to the amino acids contained in the present peptides are known in the art, and described, for example in Kuhner et al. U.S. Pat. No. 6,858,581, which describes chemically modified antimicrobial peptides.

Modulating Groups

In a tyrosinase modulator of the invention having the formula shown above, a modulating group for improved cellular uptake or efficacy or formulation may be attached directly or indirectly to the peptide of the tyrosinase inhibitor. For example, the modulating group can be directly attached by covalent coupling to the peptide or the modulating group can be attached indirectly by a stable non-covalent association. In one embodiment of the invention, the modulating group is attached to the amino-terminus of the peptide of the modulator. Alternatively, in another embodiment of the invention, the modulating group is attached to the carboxy-terminus of the peptide of the modulator.

In yet another embodiment, the modulating group is attached to the side chain of at least one amino acid residue of the peptide of the compound (e.g., through the epsilon amino group of a lysyl residue(s), through the carboxyl group of an aspartic acid residue(s) or a glutamic acid residue(s), through a hydroxy group of a tyrosyl residue(s), a serine residue(s) or a threonine residue(s) or other suitable reactive group on an amino acid side chain). Further guidance on preparing such modulating groups is found in U.S. Pat. No. 5,854,204.

The present peptides may also be conjugated to other tyrosinase inhibitors such as kojic acid (C6H6O4; 5-hydroxy-2-(hydroxymethyl)-4-pyrone) or gnetol (see *Biosci Biotechnol Biochem.* 2003 March; 67(3):663-5.)

Another modulating group for enhancing cell permeability is an amino acid sequence, which is recognized and taken up by melanocytes. D'Ursi et al., "A Membrane-Permeable Peptide Containing the Last 21 Residues of the GS Carboxyl Terminus Inhibits GS-Coupled Receptor Signaling in Intact Cells: Correlations between Peptide Structure and Biological Activity," *Mol Pharmacol* 69:727-736, 2006 disclose cell-penetrating peptides which are able to transport covalently attached cargoes such as peptide or polypeptide fragments of endogenous proteins across cell membranes. The authors coupled their peptide to the 16-residue fragment penetratin, and such fragment may be coupled to the peptides disclosed here.

Thus, the term modulating group means a small organic molecule linked to the peptide to affect its activity, either by improving its stability uptake or the like, or by providing additional tyrosinase inhibition.

In a preferred embodiment, the modifying group(s) comprises a cyclic, heterocyclic or polycyclic group. The term "cyclic group," as used herein, is intended to include cyclic saturated or unsaturated (i.e., aromatic) group having from about 3 to 10, preferably about 4 to 8, and more preferably about 5 to 7, carbon atoms. Exemplary cyclic groups include cyclopropyl, cyclobutyl, cyclopentyl, cyclohexyl, and cyclooctyl. Cyclic groups may be unsubstituted or substituted at one or more ring positions. Thus, a cyclic group may be substituted with, e.g., halogens, alkyls, cycloalkyls, alkenyls, alkynyls, aryls, heterocycles, hydroxyls, aminos, nitros, thiols amines, imines, amides, phosphonates, phosphines, carbonyls, carboxyls, silyls, ethers, thioethers, sulfonyls, sulfonates, selenoethers, ketones, aldehydes, esters, —$CF_3$, —CN, or the like.

In another preferred embodiment, the modulating group comprises a fatty acid bonded to the peptide, in order to increase uptake through the skin. Suitable fatty acids (which are meant to include the corresponding ester) include fatty acid ester emollient selected from the group consisting of methyl palmitate, methyl stearate, isopropyl laurate, isopropyl myristate, isopropyl palmitate, ethylhexyl palmitate, lauryl lactate and cetyl lactate.

The term "heterocyclic group" is intended to include cyclic saturated or unsaturated (i.e., aromatic) group having from about 3 to 10, preferably about 4 to 8, and more preferably about 5 to 7, carbon atoms, wherein the ring structure includes about one to four heteroatoms. Heterocyclic groups include pyrrolidine, oxolane, thiolane, imidazole, oxazole, piperidine, piperazine, morpholine. The heterocyclic ring can be substituted at one or more positions with such substituents as, for example, halogens, alkyls, cycloalkyls, alkenyls, alkynyls, aryls, other heterocycles, hydroxyl, amino, nitro, thiol, amines, imines, amides, phosphonates, phosphines, carbonyls, carboxyls, silyls, ethers, thioethers, sulfonyls, selenoethers, ketones, aldehydes, esters, —$CF_3$, —CN, or the like. Heterocycles may also be bridged or fused to other cyclic groups.

Formulations

The peptides of the present invention are preferably formulated into topical compositions that contain a dermatologically acceptable carrier. The phrase "dermatologically-acceptable carrier", as used herein, means that the carrier is suitable for topical application to the keratinous tissue, has good aesthetic properties, is compatible with the actives of the present invention and any other components, and will not cause any untoward safety or toxicity concerns. A safe and effective amount of carrier is from about 50% to about 99.99%, preferably from about 80% to about 99.9%, more preferably from about 90% to about 98%, and even more preferably from about 90% to about 95% of the composition.

The carrier can be in a wide variety of forms. For example, emulsion carriers, including, but not limited to, oil-in-water, water-in-oil, water-in-oil-in-water, and oil-in-water-in-silicone emulsions, are useful herein.

Preferred carriers contain an emulsion such as oil-in-water emulsions, water-in-oil emulsions, and water-in-silicone emulsions.

Emulsions according to the present invention generally contain a solution as described above and a lipid or oil. Lipids and oils may be derived from animals, plants, or petroleum and may be natural or synthetic (i.e., man-made). Preferred emulsions also contain a humectant, such as glycerin. Emulsions will preferably further contain from about 0.01% to about 10%, more preferably from about 0.1% to about 5%, of an emulsifier, based on the weight of the carrier. Emulsifiers may be nonionic, anionic or cationic. Suitable emulsifiers are disclosed in, for example, U.S. Pat. No. 3,755,560, issued Aug. 28, 1973, Dickert et al.; U.S. Pat. No. 4,421,769, issued Dec. 20, 1983, Dixon et al.; and McCutcheon's Detergents and Emulsifiers, North American Edition, pages 317-324 (1986).

The emulsion may also contain an anti-foaming agent to minimize foaming upon application to the keratinous tissue. Anti-foaming agents include high molecular weight silicones and other materials well known in the art for such use.

Suitable emulsions may have a wide range of viscosities, depending on the desired product form. Exemplary low viscosity emulsions, which are preferred, have a viscosity of about 50 centistokes or less, more preferably about 10 centistokes or less, still more preferably about 5 centistokes or less.

Preferred water-in-silicone and oil-in-water emulsions are described in greater detail in US PGPUB 20060188462 by Bissett et al., published Aug. 24, 2006, entitled "Skin care compositions containing a sugar amine."

The present peptides may be formulated in liposomes. The present peptides may be contained in liposomes according to methods, for example, as described in U.S. Pat. No. 4,944,948 to Uster, et al., entitled "EGF/Liposome gel composition and method," where one substitutes inhibitory peptide for the EGF used there. As described there, a high-viscosity aqueous dispersion of negatively charged liposomes may be prepared with liposome-entrapped peptide. The peptide/liposome composition is formed by suspending a lipid mixture typically containing equimolar amounts of neutral and negatively charged phopholipids and cholesterol in a low-conductivity aqueous medium containing peptide and a zwitterionic compound whose isoelectric point is between pH 5.5 and 8.5 to form a gel-like composition. Further exemplary guidance may be found in U.S. Pat. No. 4,485,054 to Mezei, et al., entitled "Method of encapsulating biologically active materials in multilamellar lipid vesicles (MLV)."

The present peptide tyrosinase inhibitors may also be prepared as an oral or injectable formulation. The pH of the injectable formulation is important, especially in regard to safety and comfort during injection, and especially if the preparation is supplied in a liquid formulation. A suitable formulation may contain preservatives, such as sodium benzoate, methylparaben and propylparaben, etc., and may have a pH of 6.8-8.0 at 25° C. The pH is preferably maintained by a buffer. Suitable buffering agents include acetate buffers, 2-amino-2-methyl-1-propanol, glycine buffers, phosphate buffers, (tris>hydroxymethyl-aminomethane) (TRIS) buffers, (2->N-morpholino-ethanesulfonic acid), etc. The formulation will typically also comprise a carrier as defined above. Injectable formulations are suitable for use in the treatment of melanomas and other cancers that derive from cells expressing tyrosinase, e.g., glioblastomas. Further details may be found in U.S. Pat. No. 5,773,291 to Bouchard, et al., issued Jun. 30, 1998, entitled "Non-melanotytic mammalian cell constitutively expressing biologically active human tyrosinase and use thereof." These formulations are useful with melanocytes not approachable by topical application, such as melanocytes found in non-keratinous tissue. Melanocytes are found in the basal layer of the epidermis as well as in hair follicles, the retina, uveal tract, and leptomeninges. These cells are the sites of origin of melanoma. Regarding oral formulations, an exemplary formulation may be found in US 2007/0134279.

The present peptide tyrosinase inhibitors may be used alone or in combination with each other. They may also be used in combination with other biologically active drugs or cosmeceuticals. They may be delivered by liposomes or other transdermal delivery mechanism, such as disruptive devices etc. A fatty acid chain may be conjugated to the C-terminus or N-terminus of the peptide to promote non-liposomal based delivery via lipid partition into the stratum corneum. Other lethal or suicide agents may be conjugated to the peptides allowing delivery of a lethal or suicide agent to those cells that express tyrosinase at high levels, such as melanoma cells.

Lipid peptide formulations of the present peptides are further described in U.S. Pat. No. 6,287,590 to Dasseux, issued Sep. 11, 2001, entitled "Peptide/lipid complex formation by co-lyophilization;" U.S. Pat. No. 5,543,389 to Yatvin, et al., issued Aug. 6, 1996, entitled "Covalent polar lipid-peptide conjugates for use in salves," and other references.

The length of the oligopeptides described herein, i.e., 20, or preferably 12 or less amino acids, with biological inhibitory activity against tyrosinase, has not been previously described. To date, it is believed that all agents used to inhibit tyrosinase enzyme activity vivo are non-peptide based.

Further guidance on formulating the present peptides may be found in US 20040086560 by Chaudhuri, et al., published May 6, 2004, entitled "Skin-lightening."

The present peptides may further be formulated with other ingredients useful in treating or ameliorating skin conditions, or with ingredients that reduce irritation when the peptides are administered in conjunction with an abrasive procedure. Examples of these additional ingredients, termed here "secondary treatment agents," include 1 percent vitamin K, and 1 percent hydrocortisone in a aqueous base); acne treatment formulations (e.g., salicylic acid, alcohol base buffered by witch hazel, etc.); fine lines/wrinkle treatment formulations (e.g., hyaluronic acid is an aqueous base); hydrating formulations (e.g., *calendula*, vitamins A, D, or E, or any combination, in a mineral oil base); antioxidant formulations/free radical; scavengers (e.g., vitamins A, E, and K in a mineral oil base). Other examples of product categories that may be employed alone or in combination with other compounds include, antiseptics, astringents, cleansers, pore decongestants, balms, botanicals, collagen stimulators, herbs, microemulsifiers, oxygen delivery vehicles, proteins, serums, skin firming agents, toners, and topical anesthetics. Individually named products as may be used (with associated benefit indicated parenthetically) include: aloe vera (calming); alpha hydroxy acids (peel); alphalipoic acid (antioxidant); benzoil and other peroxides (acne); ceramide (hydrator); copper (toning); copper peptide (toning); CoQ-10 (coenzyme Q-10) and other enzymes (toning); cortisone (calming); glycolic acids (peel); hyaluronic acid (collagen stimulation); hydrolipids (hydrator); lactic acids (peel); magnesium ascorbic phosphate (free radical scavenger, collagen stimulator, bleaching); niacin (vascular dilation); phospholipids (moisturization); potassium (toning, psoriasis), and salicylic acids (acne). The above ingredients are taught for use in conjunction with US PGPUB 20070088371 to Karasiuk, published Apr. 19, 2007, entitled "Microdermabrasion System and Method of Use."

As further secondary treatment agents, the tyrosinase inhibitor peptides and formulation of the present invention can also be optionally mixed with each other and with other skin whitening agents for purposes of treatment, i.e., skin lightening or whitening. For example, the skin whitening products which can be combined include but are not limited to cysteine, 4-thioresorcin, 3-aminotyrosine, 5-hydroxy-2-hydroxymethyl-γ-pyridone, fomesjaponicus and ganoderma extracts, kojic acid, glabridin, licorice extract, glycyrrhizinic acid, catharanthus roseus extract, proteoglycans, proteinase inhibitors, oligopeptides, betaines, and methyl 4-benzyloxy-2-hydroxybenzoate, 4-benzyloxy-2-hydroxybenzoic acid, etc. The present peptides may also be combined, or combined with other tyrosinase inhibitors, such as isoliquiritigenin chalcone (ILC) or 4,4'-dihydroxybiphenyl (44'-BP) (See, Kim et al., "4,4'-Dihydroxybiphenyl as a new potent tyrosinase inhibitor," *Biol Pharm Bull.* 2005 February; 28(2):323-7.)

Dosage

The term "therapeutically effective amount" is intended to mean the amount of drug sufficient to produce a tyrosinase inhibitory effect applied to a melanocyte, resulting in reduction or elimination of the production of melanin. These amounts are known in the art or may be determined by methods known in the art, and typically range from about 1 to 20,000 mg per human adult and preferably about 10 to 10,000 mg and most preferably range from about 20 to 5,000 mg of the inhibitory agent per application, depending upon the formulation chosen, and whether the tissue, such as the skin or mucous membrane is the site of action. The only upper limit on the amount of drug in the composition is that the preparation is substantially free of crystals of inhibitory agent and the amount of solvent used is not sufficient to undesirably affect the properties of the finite composition allowing it to adhere to the desired site of application. Thus, the single ingredient inhibitory peptide contains a therapeutically effective amount of inhibitory agent within the foregoing range. The concentration of peptide has been found experimentally to be suitable when extrapolated from the IC 50. In general, it is suggested that concentrations above two times IC 50 would be appropriate for prescription use; below about two times IC 50 would be suitable for over the counter use. However, formulations may contain up to about 100 times IC 50, to allow for lack of skin uptake or other losses. At twice 1050, 95% tyrosinase inhibition should be achieved. The following table is exemplary:

| Peptide | concentration mM | grams in 1 oz cream |
|---|---|---|
| KF peptide | 7.20 | 0.220 |
| YR peptide | 80 | 0.0035 |

The above formulations were prepared essentially as follows:

| INGREDIENT NAME | ACCEPTABLE RANGE | PREFERRED RANGE |
|---|---|---|
| 1. WATER | 1.00-90.00% | 30.00-70.00% |
| 2. *ALOE BARBADENSIS* LEAF JUICE | 1.00-90.00% | 5.00-60.00% |
| 3. CAPRYLIC/CAPRIC TRIGLYCERIDE | 1.00-15.00% | 5.00-10.00% |
| 4. PENTYLENE GLYCOL | 0.50-10.00% | 1.00-5.00% |
| 5. DIGLYCERIN | 0.50-20.00% | 1.00-10.00% |
| 6. BIS-ETHOXYDIGLYCOL CYCLOHEXANE 1,4-DICARBOXYLATE | 0.50-3.00% | 1.00-2.00% |
| 7. DIMETHICONE | 0.50-10.00% | 1.00-5.00% |
| 8. ETHYL ASCORBATE | 0.10-10.00% | 1.00-5.00% |
| 9. SODIUM HYALURONATE | 0.50-90.00% | 5.00-20.00% |
| 10. SODIUM PCA | 0.50-20.00% | 1.00-5.00% |
| 11. CETEARYL ALCOHOL | 0.50-5.00% | 1.00-3.00% |
| 12. DICETYL PHOSPHATE | 0.50-5.00% | 0.50-3.00% |
| 13. CETETH-10 PHOSPHATE | 0.50-5.00% | 0.50-3.00% |
| 14. *GLYCYRRHIZA GLABRA* (LICORICE) ROOT EXTRACT | 0.01-5.00% | 0.10-2.00% |
| 15. SQUALANE | 0.50-10.00% | 1.00-5.00% |
| 16. SCLEROTIUM GUM | 0.20-4.00% | 0.50-2.00% |
| 17. DECAPEPTIDE-12 | | |
| 18. BUTYLENE GLYCOL | 1.00-30.00% | 3.00-10.00% |
| 19. PANTHENOL | 0.10-5.00% | 0.50-2.00% |
| 20. ALLANTOIN | 0.01-1.00% | 0.10-0.50% |
| 21. TETRASODIUM EDTA | 0.05-2.00% | 0.10-0.50% |
| 22. CHLORPHENESIN | 0.10-1.00% | 0.10-0.50% |
| 23. CAPRYLYL GLYCOL | 0.10-2.00% | 0.50-1.00% |
| 24. PHENOXYETHANOL | 0.30-2.00% | 0.50-1.00% |

The concentration as well as the quantity of inhibitory peptide per unit area, namely per square or cubic centimeter can be varied independently in order to achieve the desired effect. Higher concentrations of inhibitory peptide base contained in a dosage form of decreased thickness will result in an application of short duration. High concentrations of the inhibitory peptide base contained in a dosage form of increased thickness (higher mg of inhibitory peptide per square or cubic centimeter) will result in potent inhibition with fast onset and long duration. Low concentrations of the inhibitory peptide base in a dosage form of decreased thickness will result in mild inhibition with longer onset and short duration. Low concentrations of the inhibitory peptide contained in a dosage form of increased thickness will have mild inhibition with longer onset and longer duration. As shown in the above explanation, the ability to vary the concentration of inhibitory peptide from very low (about 1%) to high (40% or higher) of the total composition, when combined with the ability to coat thin (about 0.001 inches) or thick (about 0.500 or more inches) enables the practitioner of the invention to vary the dosage of the system as needed for particular anatomical sites of interest.

As a general rule, in the case of a given tissue, e.g., the subepithelial layer, the peptide drug selected, the concentration and thickness and the duration of the application is determined based upon the peptide's ability to penetrate the tissue, for example the basal layer of the epidermis or mucosa, and to be at peak effectiveness within about 2 to 30 minutes. The duration of the effect of the inhibitory peptide on the tissue, for example the epidermis should range between about 2 to 240 minutes, depending on the agent selected, the concentration of the inhibitory peptide and the thickness of application. Longer or shorter durations can also be selected dependent on need, as will be apparent to one skilled in the art.

Methods of Treatment

The present peptides, formulated and/or modified as described above, may be used in a variety of treatment modalities. For example, they may be ingested, injected, or applied in conjunction with laser treatment or dermabrasion/microdermabrasion. Dermabrasion is a cosmetic medical procedure in which the surface of the skin is removed by abrasion (sanding). It is used to remove sun-damaged skin and to remove or lessen scars and dark spots on the skin. Dermabrasion units are typically diamond tipped, although aluminum crystals are also used. One approach, termed "Silk-Peel," combines a diamond tip micro-dermatome with deep delivery of solutions, which may include a whitener to improve and revitalize the skin. In a preferred method, the peptide is administered as part of a solution delivered during microdermabrasion. If the dermabrasion is carried out with a flow of fluids, which surrounds the area of skin being microabraded, the skin is both pretreated and post-treated with the vitamins, lotions, etc., as well as, in a preferred method, the present tyrosinase inhibitor peptide(s). Pretreatment can soften the area of skin treatment to be microabraded, thereby rendering exfoliation more complete and easier to accomplish, with less trauma to the skin tissues left behind, while post-treatment helps to reduce streaking and redness of the skin tissues left behind. Further details on this method of treatment may be found in U.S. Pat. No. 6,695,853 to Karasiuk issued Feb. 24, 2004, entitled "Microdermabrasion system and method of use."

The present peptides may also be used in conjunction with laser treatment. Laser treatments such as the Erbium laser vaporize various depths of damaged skin tissue. Erbium lasers are further described in U.S. Pat. No. 3,978,427. The Erbium laser procedure is performed using topical anesthetic solutions and healing is usually two to five days depending on the depth of laser energy penetration. Based on the absorption spectrum of melanin, the Q-switched ruby laser (694 nm) and the Q-switched Nd:Yag laser (1064 nm) are the lasers of choice for the treatment of hyperpigmented lesions such as lentigines and postinflammatory hyperpigmentation in combination with the present peptides.

The present peptides may be used in conjunction with a variety of radiation treatments in addition to laser treatment, such as administration of radiant energy through Rf devices, LEDs, or ultrasound. The present peptides may also be used microneedle treatment, electroporation or iontophoresis. An appropriate microneedle is described in U.S. Pat. No. 6,256, 533, entitled "Apparatus and method for using an intracutaneous microneedle array," issued on Jul. 3, 2001 to Garstein et al. Electroporation involves the application of high voltage pulses to the skin which has been suggested to induce the formation of transient pores. High voltages and short treatment durations (milliseconds) are most frequently employed. Other electrical parameters that affect delivery include pulse properties such as waveform, rate and number, and are further described in a number of publications. The technology has been successfully used to enhance the skin permeability of molecules with differing lipophilicity and size (i.e., small molecules, proteins, peptides and oligonucleotides). Iontophoresis involves the application of a low level electric current either directly to the skin or indirectly via the dosage form in order to enhance permeation of a topically applied therapeutic agent. Increased drug permeation as a result of this methodology can be attributed to either one or a combination of the following mechanisms: Electro-repulsion (for charged solutes), electro-osmosis (for uncharged solutes) and electro-perturbation (for both charged and uncharged). Several iontophoretic systems are currently under commercial development.

In addition to or included with the above mentioned disorders for which this invention can be of use, are without limitation: freckles reduction, reduction of yellow mass-tone on Asians skins and inhibition of skin, dischromia related to the aging process, as well as a reduction in redness linked to venous disorders and a reduction in UV-induced pigmentation.

As described above, a preferred method of treatment involves the lightening of skin. The present inhibitors may also be used for other treatments. Tyrosinase is an attractive target antigen for immunotherapeutic treatment of patients with melanoma because it is more homogeneously expressed than several other melanocyte differentiation antigens such as MART-1, gp100, or gp75. In two separate investigations, tyrosinase was found to be expressed in 100% of fresh melanoma specimens evaluated by immunohistochemistry or reverse transcription-polymerase chain reaction. These data indicate that tyrosinase may be an excellent target for essentially all patients with melanoma (Riley et al., *J. Immunother.*, 2001, 24, 212-220).

Tyrosinase has also been implicated in Vogt-Koyanagi-Harada (VKH) disease. VKH is a bilateral granulomatous panuveitis associated with central nervous system, auditory, and integumentary manifestations. It usually manifests with prodromal similar to asceptic meningitis, followed by posterior uveitis with exudative retinal detachments and disk hyperemia. T-cell clones established from patients with VKH disease and stimulated with tyrosinase family peptides demonstrated a predominantly proinflammatory, Th1-type T-cell response. Read et al. demonstrated that a VKH-like syndrome is inducible in rats by immunization with peptides derived from tyrosinase and other tyrosinase family proteins (Read et al., *Curr. Opin. Opthalmol.*, 2000, 11, 437-442).

EXAMPLES

Design and In Vitro Testing

Mushroom tyrosinase, L-tyrosine and other chemicals for the enzymatic reaction were obtained from Sigma-Aldrich. Short sequence peptides 1-7 were designed based on potential homology with known tyrosinase substrates. All synthetic peptides were between 3 and 10 amino acids in length and were synthesized using tBoc and/or Fmoc solid phase chemistry. Peptides were confirmed to be of research grade (>80% purity) in all cases. It is understood that research grade reagents were used for convenience, and it is preferred that the peptides be prepared to pharmaceutical grade purity, greater than 90%, preferably greater than 99% pure.

Inhibition of tyrosinase by experimental peptides was determined by colorimetric detection of dopachrome, the reaction product of the substrate L-tyrosine. Mushroom tyrosinase, L-tyrosine, and a potassium phosphate buffer (pH 6.8) were added to 96-well plates containing short sequence peptides dissolved in 5% DMSO and incubated at 37° C. The absorbance at 475 nm was measured using a BIO-TEK plate reader 30 min after reaction initiation. Each experiment was performed in triplicate on 3 separate occasions. The protocol is described in further detail in Piao et al., "Mushroom Tyrosinase Inhibition Activity of Some Chromones," Chem. Pharm. Bull. 56(3): 309-311 (2002), and in Pomerants, *J. Biol. Chem.* 238:2351-2357 (1963).

Enzyme kinetics were calculated using the Michaelis-Menton equation by observing changes in reaction velocity accompanying substrate concentrations of 0.5, 1, 2, and 4 mM L-tyrosine. Once initial reaction velocities were obtained, Lineweaver-Burke plots were created to calculate Km, Vmax, and to determine the mode of enzymatic inhibition.

IC50 Results

Seven synthetic peptides ranged in molecular weight from 321 toe 1,556 are presented below. Of the 7 peptides screened, 5 were found to possess varying inhibitory effects while 2 maintained no activity against tyrosinase. The IC50 values for these peptides ranged from ~40 µM to 8 mM. Results are given in the Table below:

| Molecular weight daltons | Agent | SEQ ID NO: | IC50 |
|---|---|---|---|
| 470.6 | VLLK | 3 | no effect |
| 1082.3 | KFEKKFEK | 1 | 3.6 mM |
| 1121.3 | KFEFKFEF | 4 | no effect |
| 1556 | YRSRKYSSWY | 2 | 40 uM |
| 1200-2400 | Poly-L lactic acid | none | no effect |

At high concentrations (15-50 mM). KFEFKFEF (SEQ ID NO: 4) abnormally increased absorbance above normal reaction values by creating a gel-like substance that interfered with colorimetric detection. Using Lineweaver-Burke plots, we found all 5 active peptides inhibited tyrosinase competitively. This was supported by the constant Vmax observed in the presence or absence of inhibitory peptides and the rescue of tyrosinase activity by addition of increasing substrate concentrations.

In conclusion, we designed synthetic short sequence peptides based on their similarity to observed properties of tyrosinase substrates. Surprisingly, we found peptides that possess varying degrees of inhibition against tryosinase.

One aspect of the present findings relates to knowledge of possible peptide modifications, including the guidance given above. In comparing the two peptides

| K | F | E | K | K | F | E | K |
|---|---|---|---|---|---|---|---|
| K | F | E | f | K | F | E | f |

It can be seen the Phe residues represented by small f are in an inactive peptide and a Lys in the corresponding positions confers activity. This shows the desirability in the above motif of having positively charged residues next to each other, as shown by the underlined KK, a property further illustrated by the SR and RN sequence in other peptides. One also observes the charged residues in YRSRKYSSWY (SEQ ID NO: 2). In addition, the presence of one or more amino acids of Tyr or similar residues (e.g., Phe or Trp) is desirable. These observations provide further guidance in designing sequences similar to those exemplified. Also, peptides may be designed to form self-assembled secondary structures, whereby multiple tyrosinase molecules may be bound by a single complex. This favors sequences having multiple tyrosine residues.

IC50 values were measured to be as low as 40 μM, a value in line with some of the efficacious tyrosinase inhibitors currently available for commercial use. The mode of inhibition was determined to be competitive in all cases. Discovery of short sequence peptides with activity against specific enzymes represents an important strategy for the development of future pharmaceutical therapies. Short sequence peptides offer several advantages over traditional pharmacological drugs and growth factors including increased skin penetration, amenability to liposomal encapsulation or lipid conjugation, and reduced toxicity. To our knowledge, this is the first report to demonstrate a significant inhibitory effect of a short sequence peptide against tyrosinase.

Stability Testing

Peptides: Five peptides, including the present YRSRKYSSWY, (SEQ ID NO: 2), and KFEKKFEK (SEQ ID NO: 1), were ordered from a commercial supplier, NeoMPS. A sixth peptide, VLLK (SEQ ID NO: 3), was used as inner standard for quantitative evaluation of other peptide stability.

HPLC/MS: A 1% solution was prepared for each peptide and sealed in a tube that was kept in ambient environment. High Performance Liquid Chromatography (HPLC) and Mass Spectroscopy (MS) were tested periodically at an approximate time range of 30 days. A fresh 1% VLLK (SEQ ID NO: 3) solution used as inner standard was prepared on the same day of each test. The amount of each peptide was determined by its peak area relative to that of VLLK (SEQ ID NO: 3).

Four peptides, including YRSRKYSSWY (SEQ ID NO: 2) and KFEKKFEK (SEQ ID NO: 1), did not show degradation for 4 months either by HPLC or MS. However, one peptide appears to start degradation during the first month as indicated by the increase of the peak area of smaller species in MS, and such degradation might be related with cysteine.

Cellular Assay

Melanogenesis suppressive activity in pigment cell is assayed in accordance with the method described in Cancer Research, Vol. 42, pp. 1994-2002 (1982) with a slight modification. $4 \times 10^4$ B-16 cells, a mouse melanoma strain, are suspended in 10 ml Eagle's MEM containing 10 v/v % fetal calf serum, transferred to 25 cm² Roux's flask, and cultured at 37° C. in the presence of 5 v/v % $CO_2$. The culture is continued for 5 days while refreshing the culture medium with fresh one additionally containing a test specimen on the starting and third days. After washing in phosphate buffer (pH 7.2) containing 0.8 w/v % saline, the cells are detached with a solution containing trypsin and EDTA, and recovered by filtration. The cells on the filter paper are then dried, and determined for the strength of reflected light at 500 nm using densitometry.

Other assays may be used in testing the present peptides. One may further screen for inhibitors of melanogenesis using assays for tyrosinase activity as described in US PGPUB 2004/0175767 by Orlow, et al., published Sep. 9, 2004, entitled "Methods and compositions that affect melanogenesis." As described there, one may cause tyrosinase to be secreted into a cellular medium for testing. Wild-type melanogenic cells grown in vitro culture will synthesize melanin inside of melanosomes as they do in vivo. In these cultured cells, tyrosinase is found predominantly in the melanosomal membrane, although some tyrosinase is also secreted. The tyrosinase that is found in the melanosomal membrane is held in place by a C-terminal transmembrane domain and has its active site disposed toward the melanosomal lumen. By contrast, in melanogenic cells inhibited for melanogenesis through either a mutation in P protein or a compound that inhibits P protein function, tyrosinase will be mislocalized. A significantly greater fraction of the cells' tyrosinase is secreted from the cells into the growth or incubation medium. Additionally, the secreted tyrosinase polypeptide will be shorter than that found in wild-type cells because it lacks its C-terminal membrane anchor. The secreted tyrosinase, however, is enzymatically active in the growth or incubation medium where it can synthesize melanin from extracellular tyrosine. Consequently, tyrosine-containing growth or incubation media from melanogenic cells that have been inhibited for melanogenesis will turn dark. The higher the concentration of tyrosine in the medium, the darker the medium becomes, and the higher the concentration of tyrosinase in the medium, the faster the medium darkens. Because melanogenic cells that are not inhibited for melanogenesis secrete significantly less tyrosinase, the tyrosine-containing growth or incubation media in which they are cultured will not become as dark.

In Vivo Assay

The peptides that exhibit significant tyrosinase inhibition in vitro may be further tested for their skin-whitening activity in vivo.

In this assay, healthy male and female volunteers (20-50 year old) receive about 0.6 J ultraviolet irradiation at two different spots in their brachial area, 2.25 cm² each, once every day for 3 days, and an inhibitory peptide is applied on either irradiated spot 3 times every day over 24 days. Thereafter, the irradiated spot with the skin-whitening agent is compared with control to estimate the degree of melanogenic suppression, i.e., skin-whitening effect.

The skin-whitening agent for such an assay may be prepared by mixing 10 parts by weight of ethanol and 0.18 parts by weight of methyl p-hydroxybenzoate together with either 0 (control), 4, 10, 16 or 40 parts by weight of 50 w/w % of either active peptide or a derivative adjusting the mixture to pH 5.5 with 10 w/w aqueous citric acid solution, and pouring refined water to the mixture to give a total amount of 100 parts by weight.

The concentration of peptide in the skin-whitening agent is therefore 0 w/w % (control), 2 w/w %, 5 w/w %, 8 w/w % or 20 w/w %.

The skin-whitening agent is applied by first soaking it in gauze, then attaching the gauze over an irradiated spot in accordance with the occlusive dressing technique.

Skin-whitening effect is determined by comparing the treated spot with control for melanogenic suppression, i.e., skin-whitening effect; grading the skin-whitening effect into either "superior", "not changed" or "inferior"; and numerating the volunteers answering "superior" (20 volunteers in each group).

Clinical Study

Patients with recalcitrant melasma (those that failed over the counter products, or HQ 4% for six months, or Tri-luma® Cream for six months) were randomized and blinded to treatment groups (vehicle and peptide for all studies described belo, Mushroom tyrosinase, L-tyrosine, hydroquinone and L-DOPA were purchased from Sigma Aldrich. YR peptide ("P4," (amino acid sequence YRSRKYSSWY (SEQ ID NO: 2), purity 94%) was synthesized by NeoMPS, Inc (San Diego, Calif., USA).

Primary human melanocytes, passage 3, were kindly obtained from Dr. Todd Ridky in the department of dermatology, Stanford University. Cells were cultured in Medium 254 (Cascade Biologics) supplemented with Human Melanocyte Growth Supplement (HMGS, Cascade Biologics). They were grown in a humidified atmosphere with 5% $CO_2$ at 37° C. Cell plating densities were arranged that those cells were in log phase of growth for the duration of incubation with test samples. Subcultures of cells were plated at a density of $4 \times 10^4$ cells/cm$^2$. Approximately 24 h later, fresh medium and test samples were added. Cells were harvested 7 d after test samples addition, replaced with fresh medium and test samples every two days.

Cell viability was determined using WST-1 Cell Proliferation Kit (Roche). Cells were plated at $1 \times 10^5$/well (24-well plates). Twenty-four hours after plating, test samples were added and cultures were incubated for an additional 7 d. At the end of the treatment period, 50 µl WST-1 was added to each well. The plates were placed at 37° C. for 4 h in the dark and the absorbance at 450 nm was read using microplate. Usually, 3 replicate wells were measured for each group to be tested. Wells containing medium but no cells served as controls. Cell viability was calculated according to the equation:

cell viability=absorbance (sample tested)/absorbance (medium only)×100%.

The concentrations of HQ tested on melanocytes were 1, 10, 100, and 1000 µM, while those of YR peptide were 1, 10, and 100 µM. Melanocytes were found dead 24 hours after the addition of HQ at either 100 or 1000 µM, confirming the cytotoxicity of HQ. Cells were found living with HQ treatment of 10 µM and below. No toxicity was observed with P4 at concentrations of up to 100 µM after treatment for 7 days.

Figure 1:
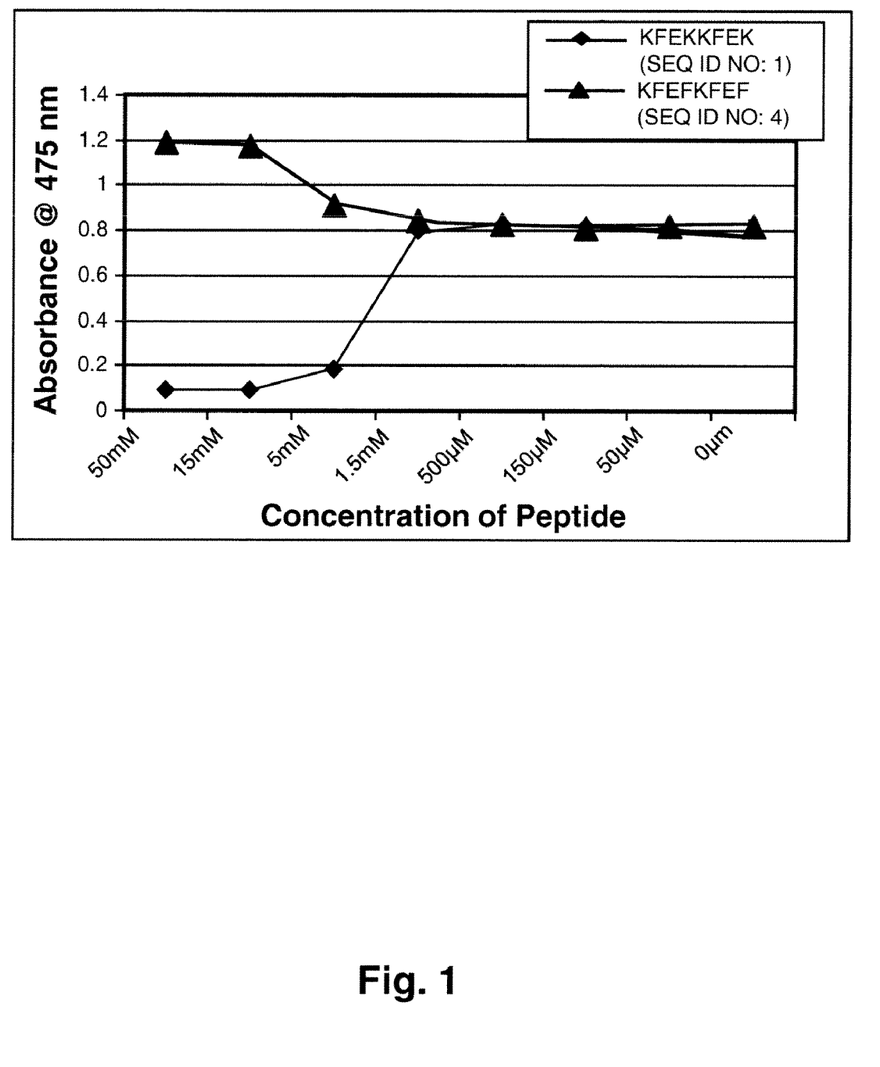
FIG. 1 is a graph showing in vitro effects of peptides KF and control peptide KFEFKFEF, (SEQ ID NO: 4), showing that only the former peptide had inhibiting activity.
Figure 2:
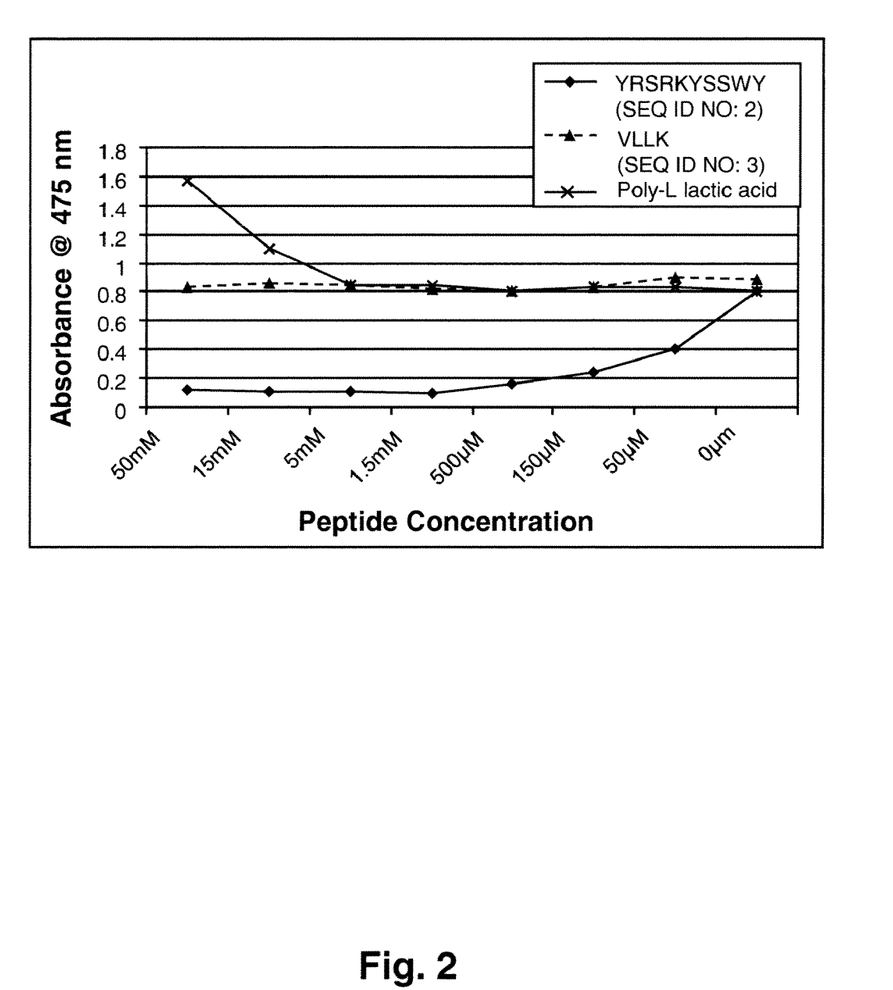
FIG. 2 is a graph of activities of YR peptide, a control, VLLK (SEQ ID NO: 3) and poly-L lactic acid, showing that only the YR peptide had inhibitory activity on tyrosinase.
Figure 3:
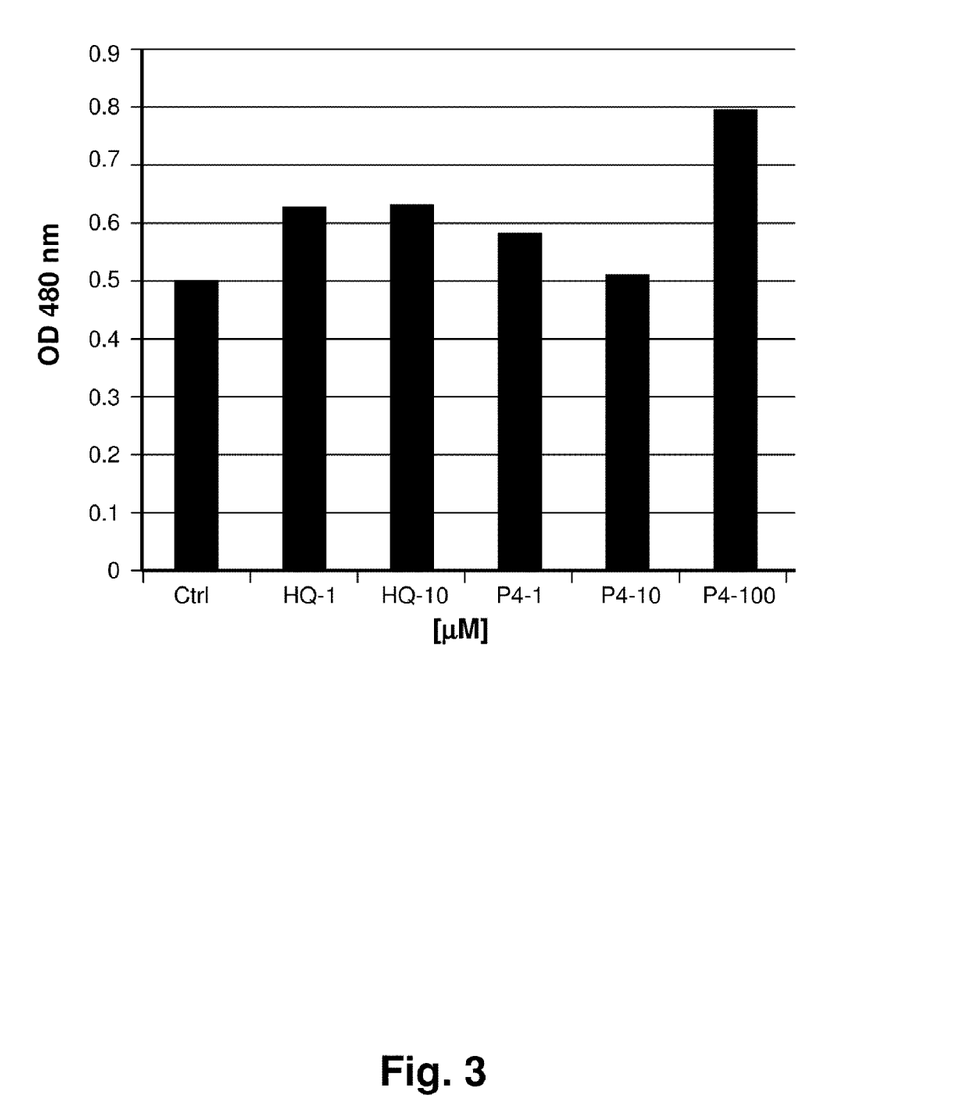
FIG. 3 is a bar graph showing proliferation rates of a control, hydroquinone (HQ) and YR peptide, designated "P4." Concentrations are given next to each peptide. It can be seen that YR peptide did not inhibit cell proliferation of melanocytes.

To exclude the possibility that the inhibitory effects of P4 on melanogenesis might be caused by the inhibition of cell growth, we compared the number of cells grown in the presence and absence of test samples. The results are shown in FIG. 3. We did not observe any inhibitory effects of the peptides on melanocyte proliferation rates. Hydroquinone also did not show inhibitory effects up to 10 µM, although higher concentrations could not be tested due to 100% cell toxicity.

Melanin Content Measurement

Human melanocytes were cultured in 6-well plates and treated with individual test samples for 7 d. After washes in PBS, cells were detached by short incubation in trypsin/EDTA (0.25%/0.1% in PBS). An aliquot was used for cell count. The remaining cells were sonicated and incubated overnight in 500 µl 1 M NaOH at 37° C., avoid light. Melanin concentrations were calculated by comparison of the OD at 475 nm of unknown samples with a standard curve obtained with synthetic melanin.

Figure 4:
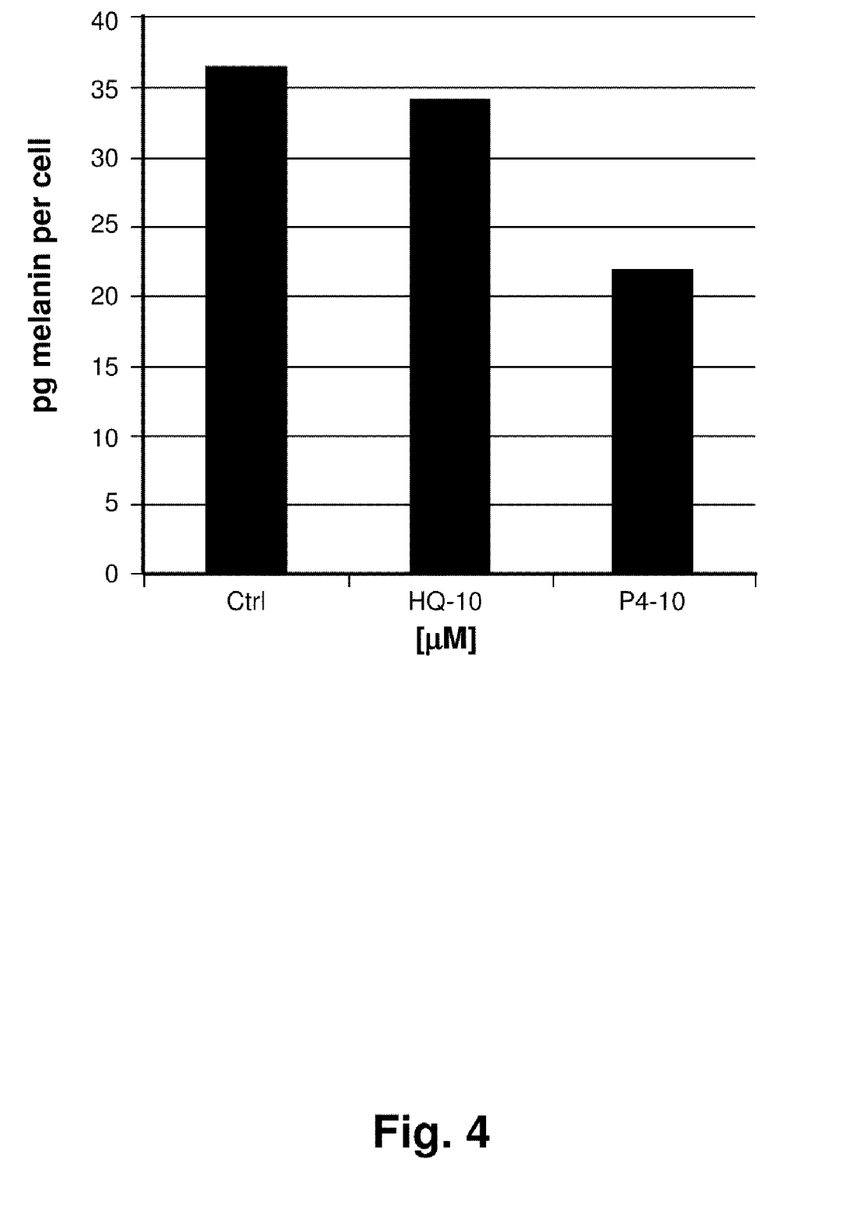
FIG. 4 is a bar graph comparing melanin content after incubation with cells of HQ and YR peptide, designated "P4." Concentrations are given next to each peptide. It can be seen that YR peptide inhibited melanin synthesis in human melanocytes.

To provide more direct evidence that the YR peptide inhibits melanogenesis, we determined its effects on melanin production in melanocytes. The contents of melanin in melanocytes treated with no addition, YR peptide (P4) or HQ for 7 days were determined with spectrophotometer and compared with melanin standard curve. The decrease in melanin content is shown in FIG. 4. Treatment with 10 µM HQ (non-toxic dose) slightly reduced melanin content. A similar concentration of YR peptide significantly reduced melanin content, to a greater extent than HQ.

Enzymatic Assay of Mushroom Tyrosinase activity on YR Peptide

Tyrosinase inhibition activity was determined in vitro using L-tyrosine as substrate with a modified method from Piao L Z, Park H R, Park Y K, Lee S K, Park J H, Park M K. 2002. Mushroom Tyrosinase Inhibition Activity of Some Chromones. *Chem Pharm Bull* 50(3): 309-311.

The concentration of enzyme, substrate and inhibitor was denoted as [E], [S] and [I], respectively. 80 microliters of 0.067 M potassium phosphate buffer (pH 6.8), 40 microliters of L-tyrosine in 0.067 M potassium phosphate buffer (pH 6.8), 40 microliters of inhibitor in 5% DMSO solution, and 40 microliters of mushroom tyrosinase solution were added to a 96-well microplate, to make the final concentration of each reagent to be: 0.2 mg/ml [S], and 96 units/ml [E], with varying [I]. 5% DMSO solution instead of an inhibitor solution was added to a blank solution and adjusted to the total volume of 200 microliters as control. The assay mixture was incubated at 37° C. The amount of dopachrome produced in the reaction mixture was measured at 475 nm in a microplate reader at different time periods. The percentage of inhibition of tyrosinase activity was calculated as follows:

$$\text{Inhibition (\%)}=[(A-B)-(C-D)]/(A-B)\times 100$$

A: absorbance of blank solution after incubation
B: absorbance of blank solution before incubation
C: absorbance of sample solution after incubation
D: absorbance of sample solution before incubation Cellular tyrosinase activity using L-DOPA as the substrate was assayed by the method of Cheng K T, Hsu F L, Chen S H, Hsieh P K, Huang H S, Lee C K, Lee M H. 2007. New Constituent from *Podocarpus macrophyllus* var. *macrophyllus* Shows Anti-tyrosinase Effect and Regulates Tyrosinase-Related Proteins and mRNA in Human Epidermal Melanocytes. *Chem. Pharm Bull* 55(5): 757-761.

Human melanocytes were cultured in 6-well plates. After treatment with individual test samples for 7 d, the cells were washed with phosphate-buffered saline (PBS) and lysed with phosphate buffer, pH 6.8, containing 1% Triton X-100. After sonication, lysates were clarified by centrifugation at 10000 g for 10 min. After determination of protein content with a Bio-Rad protein assay kit, lysates were added to 96 well culture plate containing equal amounts of protein (40 µg), and adjusted with lysis buffer to reach 150 µl in each well. 75 µl of 10 mM L-DOPA dissolved in lysis buffer was added to each well. The culture plate was incubated at 37° C. for 30 min, and then read with the spectrophotometer at 475 mm.

Tyrosinase inhibitory activity was calculated with the following formula: tyrosinase inhibition (%)=[1−(O.D.475 of sample/O.D.475 of control)]×100%.

Figure 5:
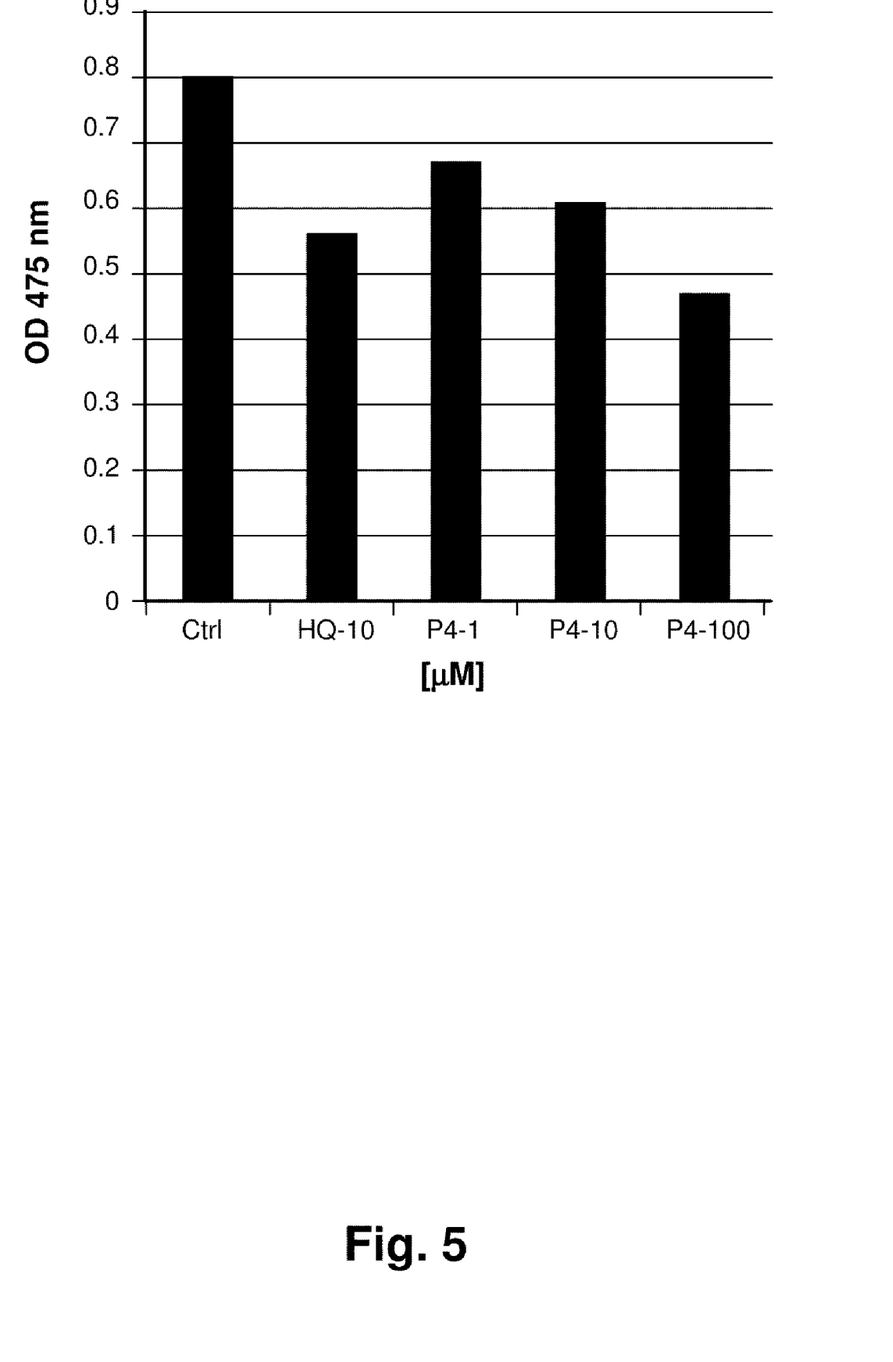
FIG. 5 is a bar graph showing tyrosinase activity after incubation with HQ and YR peptide, designated "P4." Concentrations are given next to each peptide. Inhibition of tyrosinase activity by YR peptide is comparable to that of HQ.

After centrifugation and protein calculation, certain volume of supernatant for each sample was transferred to 96 well culture plate by compensating a certain protein content in each well and adjusted the volume of each well to 150 μl with 0.067M of phosphate buffer (pH 6.8). 75 μl of 10 mM L-DOPA dissolved in phosphate buffer (pH 6.8° was added to each well. The culture plate was incubated at 37° C. for 30 min. and then read with the spectrophotometer at 475 mm. The results are shown in FIG. 5. Treatment of the melanocytes with 10 μM hydroquinone reduced cellular tyrosinase activity by 28.8%; Treatment with either peptide alone led to a dose-dependent reduction of cellular tyrosinase activity. At 1 μM, YR peptide (P4) reduced enzyme activity by 14.5%; at 10 μM, P4 decreased by 24.1%. Finally, at 100 μM, P4 decreased enzyme activity by 37.4%.

CONCLUSION

The above specific description is meant to exemplify and illustrate the invention and should not be seen as limiting the scope of the invention. Any patents or publications mentioned in this specification are indicative of levels of those skilled in the art to which the patent or publication pertains as of its date and are intended to convey details of the invention which may not be explicitly set out but which would be understood by workers in the field. Such patents or publications are hereby incorporated by reference to the same extent as if each was specifically and individually incorporated by reference, as needed for the purpose of describing and enabling the method or material referred to.

What is claimed is:

1. A method for lightening skin pigmentation in a human comprising administering to a human a tyrosinase inhibitor peptide essentially identical to one of: (a) KFEKKFEK (SEQ ID NO: 1) or (b) YRSRKYSSWY (SEQ ID NO: 2) in a therapeutically effective amount to lighten skin pigmentation.

2. The method of claim 1 wherein the peptide is essentially identical to the sequence of YRSRKYSSWY (SEQ ID NO: 2).

3. The method of claim 2 wherein the peptide YRSRKYSSWY (SEQ ID NO: 2) has between one and three substitutions in which a residue is changed to an R or K, or is changed to one of V, A, L, M or I.

4. The method of claim 1 wherein the administering comprises administering a topical preparation.

5. The method of claim 1 wherein the administering comprises administering with a secondary treatment product.

6. The method of claim 1 wherein the administering comprises administering in conjunction with a microdermabrasion process.

7. The method of claim 1 wherein the administering is simultaneous with the microdermabrasion process.

8. The method of claim 1 wherein the administering is in conjunction with a radiation process.

9. The method of claim 1 wherein the administering is in conjunction with a physical treatment carried out by an abrading device, a microneedle, an electroporation device, or an iontophoretic device.

10. The method of claim 1 wherein the administering comprises administering a topical preparation comprising at least one of kojic acid, licorice extract, and aloe.

11. A method according to claim 1 wherein said peptide is YRSRKYSSWY (SEQ ID NO: 2) in a concentration of less than 80 μM.

* * * * *